United States Patent [19]

Wu

[11] Patent Number: 5,156,165
[45] Date of Patent: * Oct. 20, 1992

[54] BIRTH CONTROL AND DISEASE PREVENTING DEVICE

[76] Inventor: Cheng M. Wu, 13726 Damian St., Cerritos, Calif. 90701

[*] Notice: The portion of the term of this patent subsequent to Jan. 28, 2009 has been disclaimed.

[21] Appl. No.: 695,584

[22] Filed: May 6, 1991

Related U.S. Application Data

[63] Continuation-in-part of Ser. No. 657,160, Feb. 15, 1991, Pat. No. 5,083,414.

[51] Int. Cl.[5] ............................................. A61F 6/00
[52] U.S. Cl. ...................................... 128/844; 128/918
[58] Field of Search ............... 128/844, 918, 846, 857, 128/859

[56] References Cited

U.S. PATENT DOCUMENTS

| | | | |
|---|---|---|---|
| 2,123,343 | 7/1938 | Rightsell | 2/21 |
| 2,138,626 | 11/1938 | Copen | 128/844 X |
| 2,548,149 | 4/1951 | Fowler | 128/295 |
| 2,591,783 | 4/1952 | Craddock | 128/132 |
| 3,677,225 | 7/1972 | Czirely | 128/132 |
| 3,759,254 | 9/1973 | Clark | 128/79 |
| 4,354,494 | 10/1982 | Hogin | 128/844 |
| 4,781,709 | 11/1988 | Grubman | 604/349 |
| 4,794,920 | 1/1989 | Robichaud | 128/844 |
| 4,808,174 | 2/1989 | Sorkin | 128/644 |
| 4,834,114 | 5/1989 | Boarman | 128/830 |
| 4,840,624 | 6/1989 | Lee | 604/349 |
| 4,867,176 | 9/1989 | Lash | 128/830 |
| 4,875,490 | 10/1989 | Quiroz | 128/830 |
| 4,887,615 | 12/1989 | Taylor | 128/844 X |
| 4,888,007 | 12/1989 | Loeb | 604/352 |
| 4,898,184 | 2/1990 | Skurkovich | 128/844 |

Primary Examiner—Robert A. Hafer
Assistant Examiner—Sam Rimell
Attorney, Agent, or Firm—Sheldon & Mak

[57] ABSTRACT

This invention relates to a birth control and disease preventing device, and more particularly to a device having a large pubic elastic shield (40) integrated about a secure-and-rolled-up (toroidal) ring (28) which is integrated about the open end (26) of a tubular portion that is configured as a conventional condom. The pubic shield has a stationary upper portion (42) and two movable lower portions (44), (46), and has a folding portion (48) between the movable portion to improve the protection of the area around the pubic and the scrotum when the user's legs are in different positions.

7 Claims, 4 Drawing Sheets

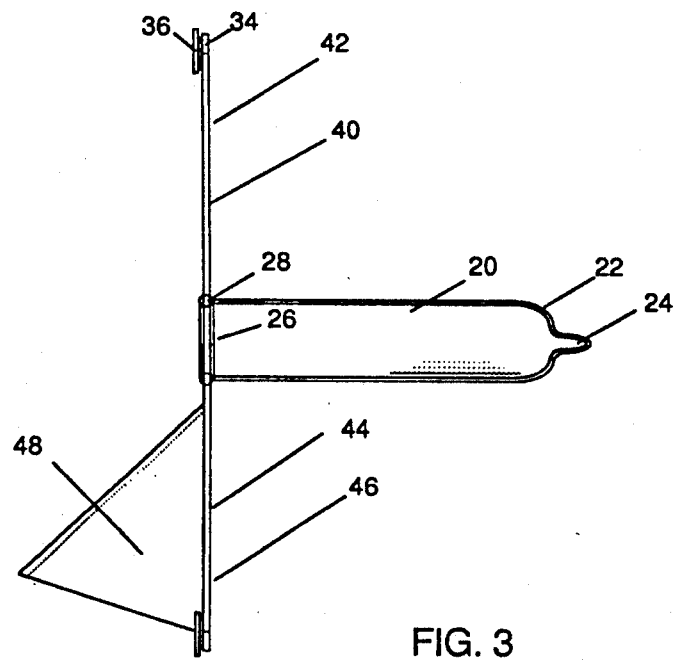
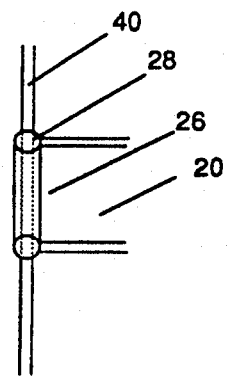 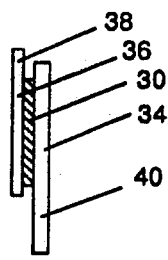 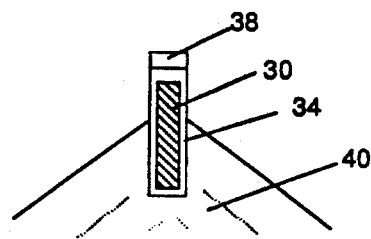
FIG. 3
FIG. 4    FIG. 5    FIG. 6

BIRTH CONTROL AND DISEASE PREVENTING DEVICE

RELATED APPLICATION

This application is a continuation-in-part of application Ser. No. 657,160, filed on Feb. 15, 1991, now U.S. Pat. No. 5,083,414, issued Jan. 28, 1992, which is incorporated herein by reference.

FIELD OF INVENTION

This invention relates to a birth control and disease preventing device, and more particularly to a device having a large elastic pubic shield integrated about a secure-and-rolled-up ring which integrated about the open end of a tubular sheath. The public shield has a stationary upper portion and two movable lower portions, and has a folding portion between the movable portions to improve the protection on the area around the pubic and the scrotum when the user's legs are in different positions.

BACKGROUND OF THE INVENTION

As the population of the earth has increased tremendously each year, birth control is an important subject to pursuit. Another important problem facing the world today is the serious consequence of the transferable diseases obtained through sexual intercourse: from the annoying skin itch, to the awful venereal diseases, and sometimes to the deadly AIDS. It can be understood that effective method is still needed to provide more efficiency for avoiding the unwanted pregnancy; and more important, to reducing the possibility of obtaining communicable sexual diseases when performing a sexual activity.

Various methods have been developed for birth control, e.g. birth control pill and IUD, etc. However, using a condom for birth control is still a simple method for those people, who may have side effects when using other birth control methods, or due to personal preference. While no contraceptive device provides 100% protection, a condom can aid in the prevention of having pregnancy when properly used. For the purpose of preventiing transmission of sexual diseases, a condom is considered simple and common useful device to achieve such goal.

Some of the prior arts have shown condoms with pubic shield having different structures and features. Those prior arts best known to the Applicant are U.S. Pat. Nos. 4,898,184; 4,888,007; 4,875,490; 4,867,176; 4,840,624; 4,834,114; 4,808,174; 4,794,920; 4,781,709; 3,759,254; 3,677,225; 2,591,783; 2,548,149; 2,123,343; and, Canadian Pat. No. 1,158,507.

In some prior art references, such as shown is U.S. Pat. Nos. 4,808,174, and 4,794,920, the protecting shields are circular but small; others, such as U.S. Pat. Nos. 4,840,624; 4,834,114, and, Canadian Pat. No. 1,158,507, the protecting shield has a general triangle shape; and others, such as U.S. Pat. Nos. 4,898,184, and 4,875,490, the protecting shield is in different shapes but having the portion near or below the genital area to be narrow and small. All the mentioned prior art references having a common feature of making the portion of the protecting shield near the scrotum area to be small typically to allow the tapes or adhesive means to be effective while the user poses his or her legs in different positions without possibly tearing the lower portion of the shield.

Other prior art reference, such as U.S. Pat. No. 4,781,709 do have a larger protecting shield; and the shield is to be worn without adhesive means at the lower portion and hang freely in front of the genital region to allow the user moving his leg freely without possibly tearing the lower portion of the shield. However, lack of fastening means at the lower portion could make the lower porting swing in uncertain positions when the user is in a face-down and crawling position.

None of the above mentioned prior art references shows a protecting shield having larger lower portioin and a folding portion near the scrotum to accompany the user's legs movement while still having adhesive means at the lower portion for maintaining fastening effort to the user's body.

Other factor is that in most of the prior art references, such as U.S. Pat. Nos. 4,875,490, 4,867,176, 4,80,624, 808,174, and, 4,794,920, they make their devices as a one-piece formation and having no securing ring between the shield and the shield; such approach may cause the device easier to slip and lose its tightness to the penis because of lacking the securing effort at the bottom of a penis. Other art references, such as that shown in U.S. Pat. Nos. 4,888,007(in his FIG. 10), 2,591,783, and Canadian Pat. No. 1,158,507, have shown devices with a ring by using a conventional condom project on a protecting shield; however, they come to two-pieces formation that require additional effort to insert the condom on the shield during a sexual activity.

This application eliminates such additional effort by integrating the shield, the securing ring, and a uniformly thick sheath as a one-piece formation. Canadian Pat. No. 1,158,507 did suggest that a condom may form an extension of and be integral with his tube (his no. 39) this is jointed to and projects forwardly and upwardly of a central portion of his sheet (his no. 13). However, such approach would make the tubular sheath having a thicker portion of double layers near the open end than the remains of portion of the tube that only has a single layer as seen in his FIG. 1. Such approach can also be seen in FIG. 10 of U.S. Pat. No. 4,888,007. This application provides a uniform thick tubular sheath with the securing ring integrated directly about the protecting shield, thus eliminating the double layer portion for providing more sensitive feeling while still having the securing ring and having the device as a one-piece formation. Such approach has not been found in the prior art references.

Among those prior art reference, nobody has shown a protecting shield having a folding portion that accompanies the user's leg movement; and nobody has shown a sheath with securing ring be integrated directly about the center portion of a shield. The market is therefore lacking of a simple device that has a protecting shield which can allow the user legs free move while still adhesive to the user body. The market is also lacking of a device in a one-piece formation having both shield and securing ring that allows the device for easier use, secure, and maintaining high sensitive feeling.

That special topic is what I present in my invention.

SUMMARY OF THE INVENTION

The invention is that by adding a large size of elastic rectangular flat and folded shield integrated about the open end of a conventional condom will reduce the skin contact and reduce the ejected sperm and fluid getting into the vagina, either by too much squeezing efforts due to vigorous motion during sexual intercourse or due to the reducing size of a penis after an ejaculation so making the condom loosing its tightness to the penis. The rectangular flat and folded shield has a stationary flat upper portion for protecting the abdomen area, and having two movable lower portions for protecting the area around the scrotum. Between the two movable portions, the protecting shield also has a folded portion allowing a user to move his legs freely while still maintaining the protection of the area around the scrotum. At the outer edge of the rectangular flat shield, there are six, but not limited to, tabs with adhesive material for holding the shield to the human body. These tabs are covered with a paper or plastic peeling sheet which will be removed to expose the adhesive to the body when the device is in use.

BRIEF DESCRIPTION OF THE DRAWING

FIG. 3 is the side-view of the invented device shown in FIG. 1.

FIG. 4 is a cross-section view of the central portion of the device shown in FIG. 1 showing the ring on a larger scale.

FIG. 5 is a cross-section view of showing a tab portion of the device shown in FIG. 1 on a larger scale.

FIG. 6 is a front view of the tab portion of FIG 5.

DETAILED DESCRIPTION OF THE INVENTION

Details of invention, and of preferred embodiments will be further understood upon reference to the drawings.

Figure 1:
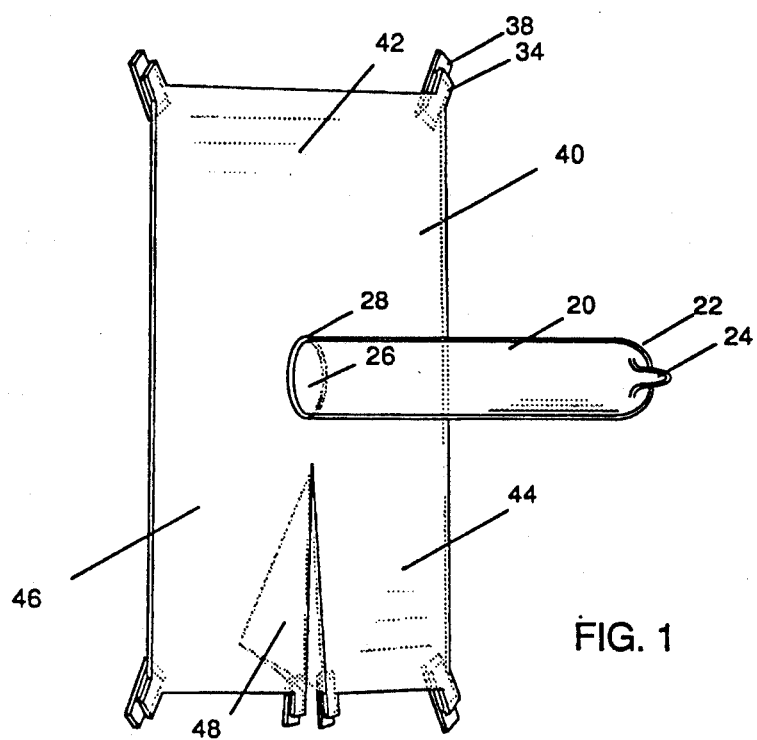
FIG. 1 is a perspective view of one preferred embodiment of the device of the invention.
Figure 2:
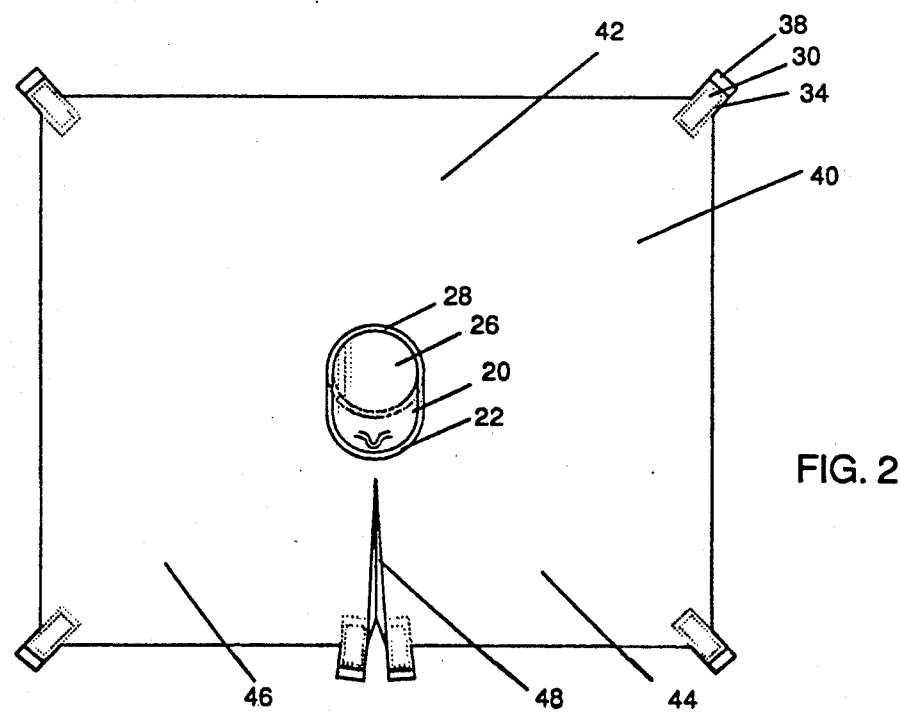
FIG. 2 is the front-view of the invented device shown in FIG. 1.
Figure 7:
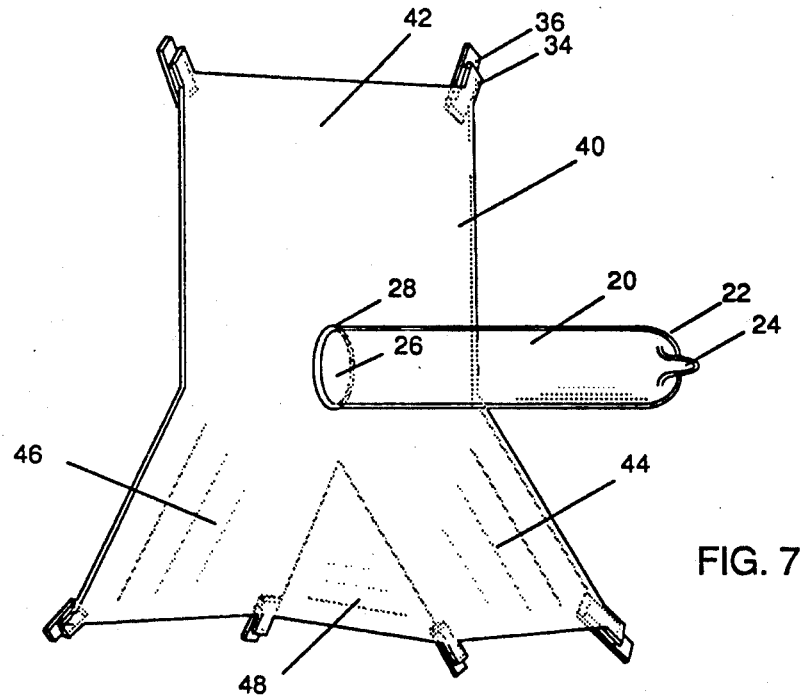
FIG. 7 is a perspective view of one preferred embodiment of the device of FIG. 1 in a display view to show the folding portion being extended out to accompany the separation of the user's legs in a walking gesture.
Figure 8:
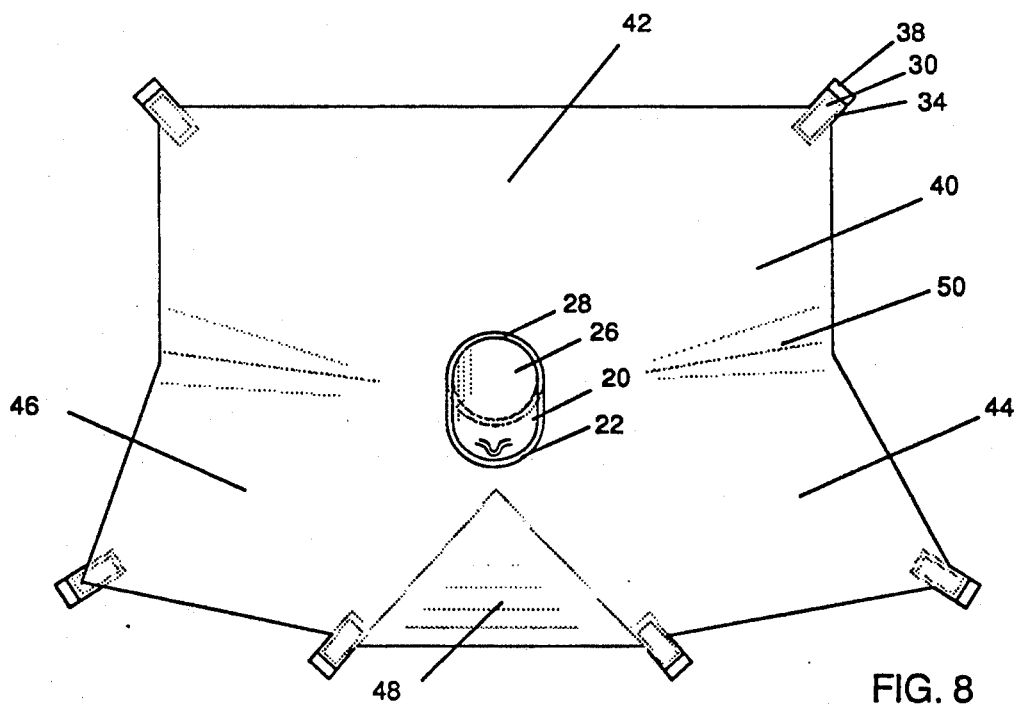
FIG. 8 is a front view of one preferred embodiment of the device of FIG. 1 in a display view to show the folding position being extended out to accompany the wide open of the user's legs in a sitting gesture.

The birth control and disease preventing device of this invention is shown in perspective view in FIG. 1. FIGS. 4, 5, and 6 show portions of the device. There is shown a condom having a resilient and flexible body construction with an elongated thin-walled tubular portion 20. The tubular portion 20 is designed to come to several sizes to receive and fit over and house a male penis, and has a closed end 22, which may or may not have a special receptacle end 24. The tubular tubular portion 20 also has an open end 26 for entering the male penis. The open end 26 is surrounding by an elastic secure-and-rolled-up or toroidal ring 28 for tightening the penis when in use, and for rolling up the device when in packaging before the use. An large elastic rectangular flat shield 40, it may comes to the shape different from a rectangle, is integrated from the toroidal ring 28. A plurality of tab portions or tabs 34, which may be six in number more or less, are integrated from the outer edge of the flat shield 40. The tabs have an area of about 2 square centimeters, more or less, with about 1 square centimeter adhesive 30 coated on it. A removable paper, or plastic peeling sheet, 36 is designed to cover the adhesive when the condom is not in use. The cover paper, or plastic peeling sheet, has a leading portion 38 for easily peeling away from the adhesive when in use. The tabs 34 are designed to be located in different positions, two for adhesive to the abdomen, two for right leg, and two for left leg. The protecting shield 40 includes an upper stationary portions 42 for protecting the pubic area, and two lower moveable portions, 44 and 46, for protecting the upper and front area of the legs. A folding portions 48, for protecting the area around the scrotum, is integrated between the two lower moveable portions, 44 and 46. The folding portion maintains the shielding effect when an user's legs are in different positions. FIG. 2 shows the front-view of the device, the two lower portions, 44 and 46, being in close position and the folding portion 48 is folded back between these two moveable portions. FIG. 3 shows the side-view of the invention, the folding portion 48 is set behind the moveable portions 44 and 46. In a normal case, the folding portion will be set between an user's legs. However, it is possible that the folding portion can be folded and rested in front of the moveable portions 44 and 46 and folded directly below the tubular tube 20 because of its flexible property. FIG. 4 shows the toroidal ring 28 integrated about the protecting shield 40 and integrated about the open end 26 of the tubular sheath 20 on a larger scale. FIGS. 5 and 6 show one of the tabs 34 on a larger scale. FIGS. 7 and 8 show the main function of the folding portion 48. In FIG. 7, the device shown in use as the user poses his legs in a walking gesture with his left leg stepping forward and right leg staying behind, the folding portion 48 stretching out and maintaining the protection below user's penis and in front of the scrotum. In FIG. 8, the device as the user is in a sitting position with his legs open, so that the folding portion 48 is stretched out. For a position shown in FIG. 8, the middle portion of the protecting shield 40 may be folding out as indicated by 50.

Figure 9:
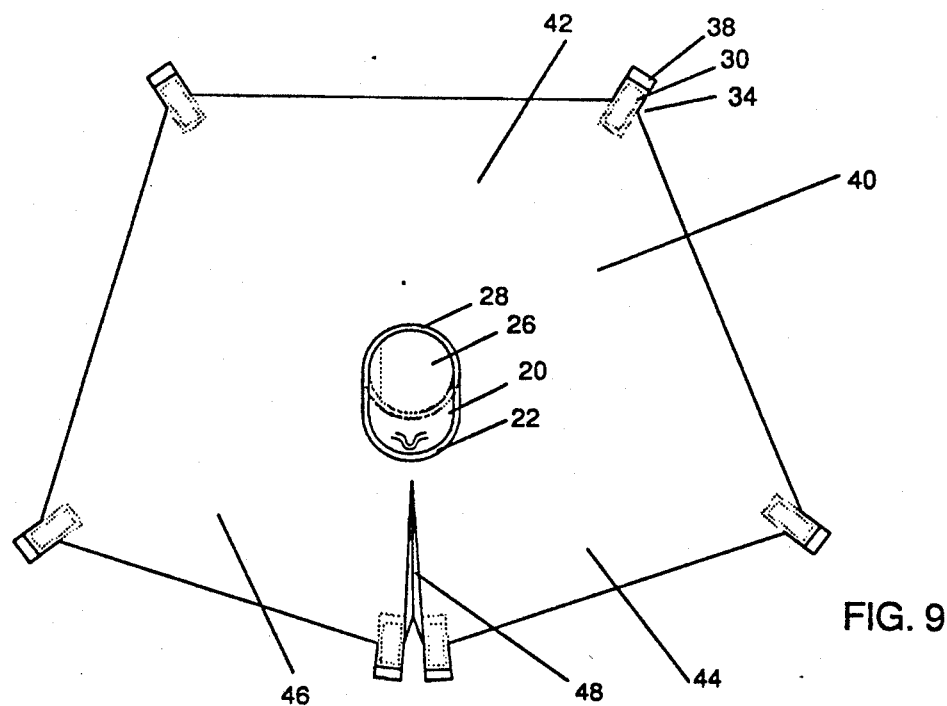
FIG. 9 is a front-view of a second embodiment of the device of FIG. 1.
Figure 10:
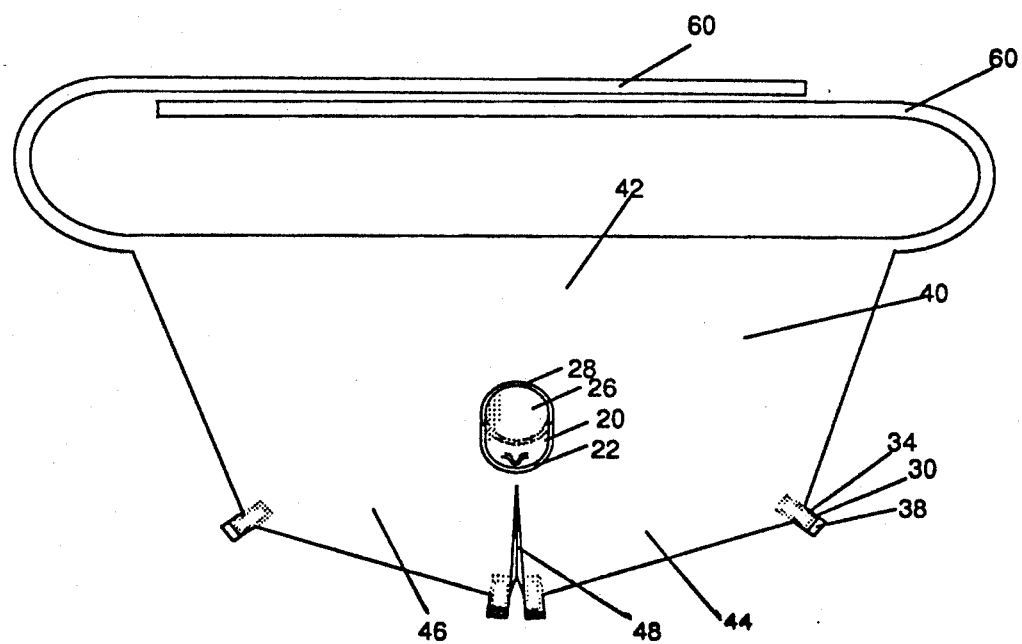
FIG. 10 is a front-view of a third embodiment of the device of FIG. 1.

A second embodiment with a different design of the protecting shield of a general pentagonal shape is shown in FIG. 9. FIG. 10 shows a third embodiment with different shape and different adhesive means that uses two long strands, or plastic tapes for fastening the device to the user's loins.

From the foregoing mentioned figures, although a limited number of embodiments of the invention have been described in detail, it should be realized that modifications and other embodiments incorporating the invention features may be constructed. It should be realized that the features shown in these figures can be combined and modified. The folding portion 48 can be made in different shape and can be folded in different packaging positions, i.e., single folded or multiple folded. The second embodiment, FIG. 9 has a shield design different from the first embodiment, FIG. 2. The third embodiment features two long strands or tapes for fastening and has a different shield shape. A combination of any of these features, or modifying, can easily create another embodiment within the scope of the invention. It is intended that the foregoing disclosures and drawings shall be considered only as illustrations of the principles of the invention.

For my invention, the material herein specified are not critical, and any material having similar characteristics, such as latex or rubber having stretchable and flexible ability, would be capable of making such a condom. Any material used for making a conventional condom is suitable to make this invention.

The overall length of the tubular tubes and the size of the rectangular flat shield is conventional. In the embodiment of FIG. 1, the length of the tubular is about 15 to 22 centimeters and the width, when the tubular lies flat on the table is about 5 to 6 centimeters. The rectangular flat shield is about 800 to 1200 square centimeters for the first preferred embodiment. While specified dimensions are given herein alone, it should be clear that the dimensions are given by the way of example only, and that variations of other dimensions can be used, as disired, depending upon the size of human penis and body.

From the foregoing, it should be evident that the invention provides a new and improved device. The device will provide both more effective birth control and provides more protection against the transmission of venereal diseases during copulation when compared with conventional condoms made by the same material.

I claim:

1. A birth control and disease preventing device made from a flexible and water-impervious material, comprising:
   (a) a solid toroidally shaped ring portion, the ring portion being sized for anchoring onto the penis of a user during coitus;
   (b) a thin tubular sheath portion having an open proximal end and a closed distal end, the proximal end being sealingly integrally formed with the ring portion, the sheath portion being sized to house the penis; and
   (c) a thin protecting shield portion sealingly integrally formed with the ring portion and extending outwardly therefrom for preventing skin contact of lower abdomen and thigh portions between sexual partners, the ring portion forming an opening in the shield portion, the shield and sheath portions being rollable onto the ring portion for compactly configuring the device prior to use thereof.

2. The device of claim 1, wherein the shield portion is formed with outer corner extremities, the device further comprising means for fastening the corner extremities of the shield portion to the body of a male user during coitus.

3. The device of claim 1, wherein the ring portion has an outside diameter of approximately 3 centimeters and an inside diameter of approximately 2 centimeters.

4. The device of claim 3, wherein the outside diameter of the ring portion is approximately equal to the diameter of the open proximal end of the sheath portion, the opening in the shield portion being approximately centrally located in the shield portion, the diameter of the opening being approximately equal to the outside diameter of the ring portion.

5. The device of claim 1, wherein the shield portion has an upper stationary portion for protecting the pubic and abdomen area of the user, the shield portion also being divided below the ring portion between two movable portions for protecting respective upper front thigh areas of the user, the shield portion further having a connecting portion joining inside extremities of the lower portions for protecting a scrotum and upper inner thigh area of the user while permitting movement of the two movable portions corresponding to independent movement of the user's thighs.

6. The device of claim 5, wherein the connecting portion has a generally triangularly shaped pleated skirt-like folding configuration being integrated along the two lower movable portions and forming a retractable and extendable dynamic protecting shield for accommodating the user's thighs in different poses and positions, whereby the connecting portion assumes a folded retract condition when the user's thighs are close to each other and assumes an open, spread out condition when the user's thighs are open and apart.

7. A birth control and disease preventing device made from a flexible and water-impervious material, comprising:
   (a) a solid toroidally shaped ring portion, the ring portion being sized for anchoring onto the penis of a user during coitus;
   (b) a thin tubular sheath portion having an open proximal end and a closed distal end, the proximal end being sealingly integrally formed with the ring portion, the sheath portion being sized to house the penis, the diameter of the open proximal end of the sheath portion being approximately equal to the outside diameter of the ring portion;
   (c) a thin protecting shield portion sealingly integrally formed with the ring portion and extending outwardly therefrom to outer corner extremities of the shield portion for preventing skin contact of lower abdomen and thigh portions between sexual partners, the ring portion forming an approximately centrally located opening in the shield portion, the diameter of the opening being approximately equal to the outside diameter of the ring portion, the shield portion having an upper stationary portion for protecting the pubic and abdomen area of the user, the shield portion also being divided below the ring portion between two movable portions for protecting respective upper front thigh areas of the user, the shield portion further having a connecting portion joining inside extremities of the lower portions for protecting a scrotum and upper inner thigh area of the user while permitting movement of the two movable portions corresponding to movement of the user's thighs, the shield and sheath portions being rollable onto the ring portion for compactly configuring the device prior to use thereof; and
   (d) means for fastening the corner extremities of the shield portion to the body of a male user during coitus.

* * * * *